US011298862B2

(12) United States Patent
Jones et al.

(10) Patent No.: US 11,298,862 B2
(45) Date of Patent: Apr. 12, 2022

(54) MOLDS FOR INTERNAL HERMETIC CONNECTOR SEALS

(71) Applicant: Medtronic, Inc., Minneapolis, MN (US)

(72) Inventors: Curtis L. Jones, Onamia, MN (US); David A. Bates, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 211 days.

(21) Appl. No.: 16/470,935

(22) PCT Filed: Mar. 21, 2018

(86) PCT No.: PCT/US2018/023471
§ 371 (c)(1),
(2) Date: Jun. 18, 2019

(87) PCT Pub. No.: WO2018/222246
PCT Pub. Date: Dec. 6, 2018

(65) Prior Publication Data
US 2020/0078995 A1 Mar. 12, 2020

Related U.S. Application Data

(60) Provisional application No. 62/512,502, filed on May 30, 2017.

(51) Int. Cl.
*B29C 45/26* (2006.01)
*H01R 13/52* (2006.01)
(Continued)

(52) U.S. Cl.
CPC ...... *B29C 45/2606* (2013.01); *B29C 45/1459* (2013.01); *B29C 45/14065* (2013.01);
(Continued)

(58) Field of Classification Search
CPC .................. B29C 45/2606; B29C 45/14065
See application file for complete search history.

(56) References Cited

U.S. PATENT DOCUMENTS 4,445,511 A * 5/1984 Cowdery ............. A61N 1/3752
607/37
6,817,905 B2 * 11/2004 Zart ..................... A61N 1/3752
439/736
(Continued)

FOREIGN PATENT DOCUMENTS

CN   205522281 U   8/2016
GB     2122428 A   1/1984

OTHER PUBLICATIONS

International Search Report and Written Opinion of International Application No. PCT/US2018/023471, dated Oct. 24, 2018, 13 pp.

*Primary Examiner* — Benjamin A Schiffman
(74) *Attorney, Agent, or Firm* — Shumaker & Sieffert, P.A.

(57) ABSTRACT

An example mold assembly includes a first core, a second core, and a retaining cap. The first core defines an insert seat configured to receive a mold insert. The first core and the second core are configured to define a mold volume adjacent the mold insert. The retaining cap is disposed about a curved end portion defined by the second core, and defines a curved cap surface in contact with the curved end portion. The retaining cap is configured to secure the second core at a predetermined orientation relative to the first core within predetermined tolerances. An example technique includes positioning a mold insert in the mold assembly, disposing the retaining cap about the second core, securing the second core at a predetermined orientation relative to the first core within predetermined tolerances, and depositing mold material within the mold volume.

33 Claims, 6 Drawing Sheets

(51) Int. Cl.
  *B29C 45/14* (2006.01)
  *B29C 45/34* (2006.01)
  *H01R 43/00* (2006.01)
  *B29C 45/36* (2006.01)
  *B29C 45/27* (2006.01)
  *A61N 1/36* (2006.01)
  *A61N 1/362* (2006.01)
  *B29L 31/26* (2006.01)
  *B29C 33/12* (2006.01)
  *B29C 33/30* (2006.01)

(52) U.S. Cl.
  CPC .............. *B29C 45/26* (2013.01); *B29C 45/27* (2013.01); *B29C 45/34* (2013.01); *B29C 45/36* (2013.01); *H01R 13/5219* (2013.01); *H01R 13/5224* (2013.01); *H01R 43/005* (2013.01); *A61N 1/362* (2013.01); *A61N 1/3605* (2013.01); *B29C 33/123* (2013.01); *B29C 33/303* (2013.01); *B29C 33/304* (2013.01); *B29C 2045/14122* (2013.01); *B29L 2031/26* (2013.01)

(56) References Cited

U.S. PATENT DOCUMENTS

| | | |
|---|---|---|
| 7,717,754 B2 | 5/2010 | Ries et al. |
| 9,362,660 B2 | 6/2016 | Ries et al. |
| 2003/0069612 A1 | 4/2003 | Zart et al. |
| 2011/0270363 A1 | 11/2011 | Schramm et al. |
| 2015/0018922 A1 | 1/2015 | Nolan et al. |
| 2015/0094792 A1 | 4/2015 | Kane et al. |

* cited by examiner

MOLDS FOR INTERNAL HERMETIC CONNECTOR SEALS

This application is a U.S. National Stage entry under 35 U.S.C. § 371 of International Application No. PCT/US2018/023471, filed Mar. 21, 2018, which claims the benefit of U.S. Provisional Application No. 62/512,502, filed on May 30, 2017. The entire contents of each of these applications is incorporated herein by reference.

TECHNICAL FIELD

This disclosure relates to assemblies and techniques for manufacturing internal hermetic lead connectors for implantable medical devices, in particular, for molding seals in internal hermetic lead connectors.

BACKGROUND

Implantable medical devices (IMDs), for example, neurostimulators, pacemakers and defibrillators, may include one or more leads and electrodes disposed on the leads for delivering electrical stimulation to muscles or nerves or for sensing response of tissue to the stimulation. IMDs may include a hermetically sealed housing containing a power source, for example, a battery, and control electronics for controlling the stimulation that may be coupled to a lead connector block.

The lead connector block may couple a lead to the control electronics, either directly or through a lead extension. The lead connector block may include electrical contacts for electrically coupling the electrodes via the lead to the control electronics. While the lead connector block provides electrical coupling between the control electronics and the lead, the lead connector block also maintains a seal between the lead and the IMD housing to prevent body fluids from entering the housing, to prevent contamination and short-circuiting.

SUMMARY

In some examples, an example mold assembly includes a first core, a second core, and a retaining cap. The first core defines an insert seat configured to receive a mold insert. The second core defines a pin portion configured to contact at least a first insert surface defined by the mold insert. The second core defines a curved end portion opposing the pin portion. The first core and the second core are configured to define a mold volume adjacent the mold insert. The retaining cap is disposed about the curved end portion defined by the second core. The retaining cap defines a curved cap surface in contact with the curved end portion. The retaining cap secures the second core at a predetermined orientation relative to the first core within predetermined tolerances.

In some examples, an example technique includes positioning a mold insert on an insert seat defined by a first core of a mold assembly. The example technique includes disposing a retaining cap about a curved end portion defined by a second core of the mold assembly. The example technique includes securing the second core at a predetermined orientation relative to the first core within predetermined tolerances such that a pin portion defined by the second core contacts at least a first insert surface defined by the mold insert and such that the first core and the second core define a mold volume adjacent the mold insert. The example technique includes depositing mold material within the mold volume adjacent the mold insert.

Clause 1: A mold assembly comprising: a first core defining an insert seat configured to receive a mold insert; a second core defining a pin portion configured to contact at least a first insert surface defined by the mold insert, wherein the second core defines a curved end portion opposing the pin portion, and wherein the first core and the second core are configured to define a mold volume adjacent the mold insert; and a retaining cap disposed about the curved end portion defined by the second core, wherein the retaining cap defines a curved cap surface in contact with the curved end portion, and wherein the retaining cap is configured to secure the second core at a predetermined orientation relative to the first core within predetermined tolerances.

Clause 2: The mold assembly of clause 1, wherein the curved cap surface of the retaining cap is substantially concave, and wherein the curved end portion of the second core is substantially convex and conforms to the curved cap surface.

Clause 3: The mold assembly of clause 1 or 2, wherein the curved cap surface of the retaining cap and the curved end portion of the second core define a ball joint configured to allow the second core to pivot relative to the retaining cap while securing the second core at the predetermined orientation within the predetermined tolerances.

Clause 4: The mold assembly of any one of clauses 1 to 3, wherein the first core defines a first core pin, wherein the first core comprises a first core sleeve surrounding at least a portion of the first core pin, and wherein one or both of the first core pin and the first core sleeve define the insert seat.

Clause 5: The mold assembly of clause 4, wherein the first core pin abuts the pin portion defined by the second core.

Clause 6: The mold assembly of clause 4 or 5, wherein the first core sleeve is configured to restrict motion of the first core to motion along or about a longitudinal axis defined by the first core sleeve.

Clause 7: The mold assembly of any one of clauses 4 to 6, wherein the first core sleeve is secured to the first core pin by an interference fit between an outer first core pin surface defined by the first core pin and an inner core sleeve surface defined by the first core sleeve.

Clause 8: The mold assembly of any one of clauses 1 to 7, further comprising a retaining sleeve defining a first inner sleeve surface disposed about at least the insert seat of the first core and a second inner sleeve surface disposed about at least the pin portion of the second core, and wherein the retaining cap defines a retaining surface secured about an outer sleeve surface defined by the retaining sleeve.

Clause 9: The mold assembly of clause 8, wherein the retaining sleeve secures the first core to maintain the predetermined orientation of the second core relative to the first core within the predetermined tolerances.

Clause 10: The mold assembly of clause 8 or 9, wherein the retaining cap is secured to the retaining sleeve by an interference fit between the retaining surface and the outer sleeve surface.

Clause 11: The mold assembly of clause 8 or 9, wherein the retaining cap is secured to the retaining sleeve by a threaded fit between a first thread defined by the retaining surface and a second thread defined by the outer sleeve surface.

Clause 12: The mold assembly of any one of clauses 8 to 11, wherein the retaining sleeve defines an annular landing, and wherein the first core defines an annular lip, wherein the annular landing secures the annular lip.

Clause 13: The mold assembly of clause 12, wherein the first core sleeve of the first core defines the annular lip.

Clause 14: The mold assembly of clause 12 or 13, wherein the annular landing is between the first inner sleeve surface and the second inner sleeve surface.

Clause 15: The mold assembly of any one of clauses 1 to 14, wherein the first core defines at least one overflow vent configured to remove air from the mold volume.

Clause 16: The mold assembly of clause 15, wherein one or both of the first core sleeve or the first core pin defines the at least one overflow vent.

Clause 17: The mold assembly of any one of clauses 1 to 16, wherein the second core and the retaining cap define a runner fluidically connected to the mold volume to admit mold material into the mold volume.

Clause 18: The mold assembly of clause 17, wherein one or both of the first core and the second core define a fan gate fluidically connected to the mold volume and to the runner to admit mold material from the runner into the mold volume.

Clause 19: The mold assembly of any one of clauses 1 to 18, wherein one or both of the first core and the second core define a fan gate fluidically connected to the mold volume to admit mold material into the mold volume.

Clause 20: The mold assembly of any one of clauses 1 to 19, wherein the mold insert comprises a first ferrule, a second ferrule, and an insulator, wherein the insulator secures the first ferrule to the second ferrule, and wherein the insulator electrically isolates the first ferrule from the second ferrule.

Clause 21: The mold assembly of any one of clauses 1 to 20, wherein the mold insert comprises an internal hermetic connector segment.

Clause 22: The mold assembly of any one of clauses 1 to 21, further comprising the mold insert.

Clause 23: The mold assembly of any one of clauses 1 to 22, further comprising a mold material occupying the mold volume.

Clause 24: A method comprising: positioning a mold insert on an insert seat defined by a first core of a mold assembly; disposing a retaining cap about a curved end portion defined by a second core of the mold assembly; securing the second core at a predetermined orientation relative to the first core within predetermined tolerances such that a pin portion defined by the second core contacts at least a first insert surface defined by the mold insert and such that the first core and the second core define a mold volume adjacent the mold insert; and depositing mold material within the mold volume adjacent the mold insert.

Clause 25: The method of clause 24, further comprising allowing the mold material to set to form a molded seal secured to the mold insert.

Clause 26: The method of clause 24 or 25, further comprising maintaining one or both of a temperature or a pressure within the mold volume within a respective predetermined temperature range or a respective predetermined pressure range.

Clause 27: The method of any one of clauses 24 to 26, further comprising, after setting of the mold material: separating the first core and the second core; and removing the mold insert including the molded seal from the mold assembly.

Clause 28: The method of any one of clauses 24 to 27, further comprising orienting one or both of the first core or the second core such that a first core pin defined by the first core abuts the pin portion defined by the second core, and such that one or both of the first core pin and a first core sleeve surrounding at least a portion of the first core pin define the insert seat.

Clause 29: The method of clause 28, further comprising securing the first core sleeve to the first core pin by an interference fit between an outer first core pin surface defined by the first core pin and an inner core sleeve surface defined by the first core sleeve.

Clause 30: The method of any one of clauses 24 to 29, wherein securing the second core at the predetermined orientation within predetermined tolerances relative to the first core comprises: disposing a first inner sleeve surface defined by a retaining sleeve about at least the insert seat of the first core; disposing a second inner sleeve surface defined by the retaining sleeve about at least the pin portion of the second core; and securing a retaining surface defined by the retaining cap about an outer sleeve surface of the retaining sleeve such that a curved cap surface defined by the retaining cap contacts the curved end portion defined by the second core.

Clause 31: The method of clause 30, wherein securing the retaining surface defined by the retaining cap about the outer sleeve surface defined by the retaining sleeve comprises providing an interference fit between the retaining surface and the outer sleeve surface.

Clause 32: The method of clause 30, wherein securing the retaining surface defined by the retaining cap about the outer sleeve surface defined by the retaining sleeve comprises threading the retaining surface over the outer sleeve surface.

Clause 33: The method of any one of clauses 30 to 32, further comprising securing an annular lip defined by the first core sleeve to an annular landing defined by the retaining sleeve.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Example mold assemblies and techniques according to the disclosure may be used to provide a seal on an internal hermetic connector (IHC) segment portion to form an IHC segment. IHC segments may be assembled to form an IHC assembly. A lead connector block of a medical device may include an IHC assembly to provide a hermetically sealed conductive path between a medical device and an external component. For example, an implantable medical device may include an IHC assembly to provide a hermetically sealed conductive pathway between circuitry within a sealed housing of the medical device and a lead outside the sealed housing.

Figure 1:
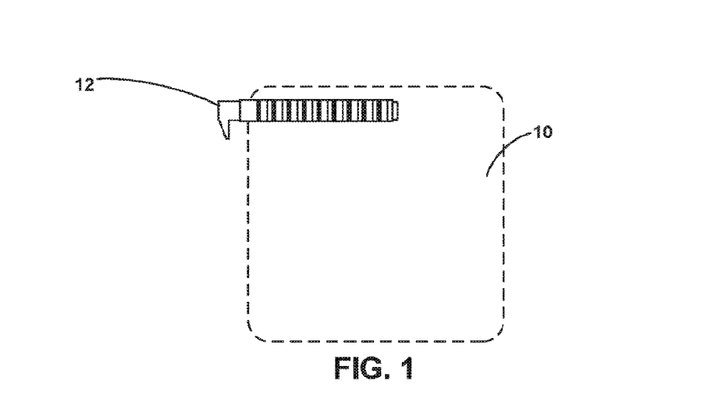
FIG. 1 is a schematic and conceptual side view of an example medical device including an example internal hermetic connector assembly.

FIG. 1 is a schematic and conceptual side view of an example medical device 10 including an example internal hermetic connector (IHC) assembly 12. IHC assembly 12 provides a conductive path extending between circuitry (not shown) within a hermetically sealed housing of medical device 10 and a lead (not shown) outside the hermetically sealed housing. The conductive path may include a conductor pin or terminal that is electrically insulated from the hermetically sealed housing. IHC assembly 12, while providing a conductive path, also maintains the seal between medical device 10 and its environment. In examples in which medical device 10 is implanted in a patient, such sealing may avoid problems arising from contamination and short-circuiting by body fluids adjacent implanted medical device 10.

In some examples, IHC assembly 12 may substantially reduce lead interconnect volume of medical device 10 connected to a lead by combining the functionality of a lead connector block and an electrical feedthrough into a relatively compact modular component. IHC assembly 12 may be formed by stacking and joining a number of IHC segments.

Figure 2:
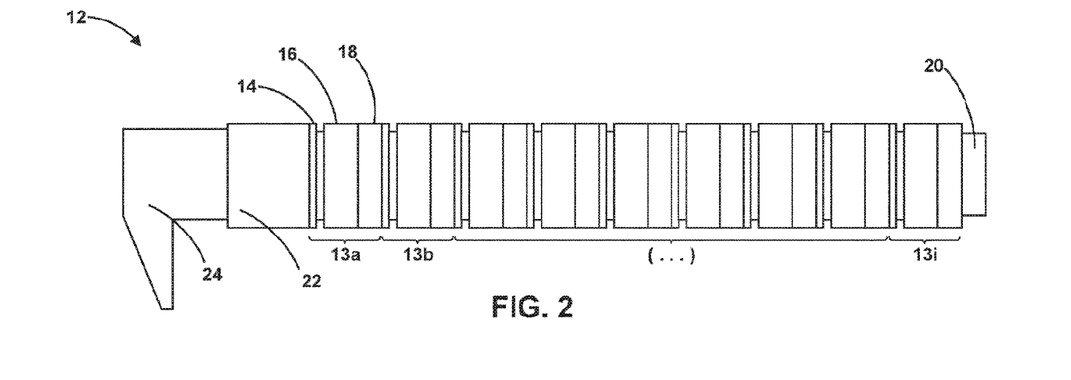
FIG. 2 is a schematic and conceptual side view of the example internal hermetic connector assembly of FIG. 1.

FIG. 2 is a schematic and conceptual side view of internal hermetic connector assembly 12 of FIG. 1. IHC assembly 12 may assume the form of a hermetic cylinder including a series of modular IHC segments 13, for example, 13a to 13i, as shown in FIG. 2. IHC assembly 12 may include a fewer or greater number of IHC segments than shown in FIG. 2. Each IHC segment 13 may define an internal void, and the internal voids combine to define a channel or bore defined by IHC assembly 12. An end of a lead may be introduced into the channel, and electrical contacts at the end of the lead may be coupled with respective interior electrical contacts within an interior of IHC assembly 12. An exterior of IHC assembly 12 may have respective outer electrical contacts coupled with the interior electrical contacts. For example, each respective IHC segment 13 may include one or more metal or alloy ferrules 14 and 16 and an electrical spring contact 18 that provides a conductive path between the interior of IHC assembly 12 electrically coupled to the lead and the exterior of IHC assembly 12 electrically coupled to circuitry within medical device 10. Thus, IHC assembly 12 may allow an external component such as a lead to be electrically coupled to circuitry within medical device 10 while maintaining a hermetic seal between the interior of medical device 10 and an environment external to medical device 10.

IHC assembly 12 may include additional components, for example, an end pin 20 disposed at one end of IHC assembly 12, a collar 22, and a lead connector 24 defining an opening for introducing a lead into IHC assembly 12.

Figure 3:
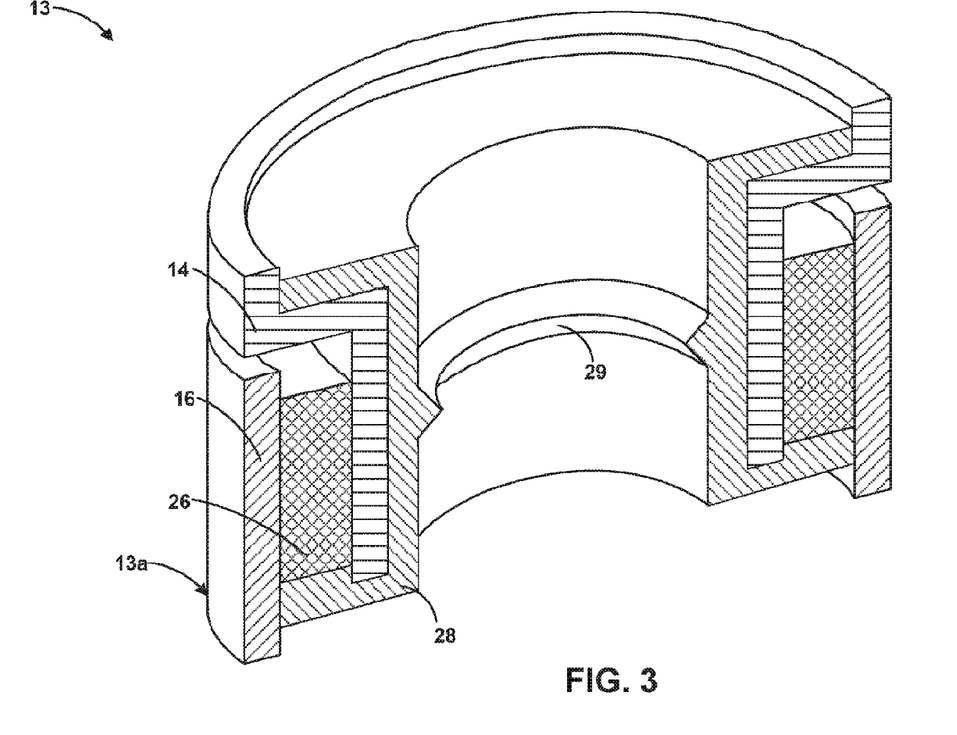
FIG. 3 is a schematic and conceptual side view of an example internal hermetic connector segment of the internal hermetic connector assembly of FIG. 2.

FIG. 3 is a schematic and conceptual side view of an internal hermetic connector segment 13, for example, internal hermetic connector segment 13a of IHC assembly 12 of FIG. 2. IHC segment 13 includes a first ferrule 14, a second ferrule 16, and an insulator 26 between the first ferrule and the second ferrule 16. One or both of the first and second ferrules 14 and 16 may be annular, or include annular segments, or have any suitable shape for surrounding a lead. One or both of the first and second ferrules 14 and 16 may include the same or different conductive material. The conductive material may include a metal or an alloy. In some examples, the metal or the alloy may include titanium, steel (for example, stainless steel), nitinol, niobium, platinum iridium, MP35N alloy, platinum-iridium alloy, or any other metal or alloy suitable for medical or surgical applications or combinations thereof. In some examples, the metal or alloy consists of titanium. The titanium may be a medical grade titanium, for example, Grade 5 titanium.

Insulator 26 may include any suitable rigid or semi-rigid insulating material, for example, glass or ceramic. The glass may include LaBor-4 glass material, which is a glass about 30% $B_2O_3$, about 20% CaO, about 20% MgO, about 5% $La_2O_3$, about 10% $SiO_2$ and about 15% $Al_2O_3$, wherein percentages are mole percentages, and the CaO and/or MgO may be replaced with corresponding amounts of SrO. In some examples, the glass may include Ta-23 glass (nominally, 45 weight % $SiO_2$, 20 weight % $Al_2O_2$, 8 weight % $B_2O_3$, 12 weight % CaO, 6 weight % MgO and 2 weight % $La_2O_3$), Cabal-12 glass (aluminum oxide [$Al_2O_3$]:boron oxide [$B_2O_3$]:calcium oxide [CaO]:magnesium oxide [MgO], for example, with relative approximate concentrations of 20:40:20:20 (mol %), and sodium oxide ($Na_2O$), potassium oxide ($K_2O$), silicon oxide ($SiO_2$) and arsenic oxide ($As_2O_3$) at maximum concentrations of thousands parts per million), or lead-free phosphate glasses.

In some examples, insulator 26 consists of glass. The insulating material of insulator 26 may electrically insulate first ferrule 14 from second ferrule 16. Insulator 26 may be annular, or include annular segments, or may have any suitable shape or geometry, for example, a shape or geometry complementary to one or more surfaces defined by first or second ferrules 14 or 16. In the example shown in FIG. 3, first ferrule 14, second ferrule 16, and insulator 26 are annular and co-concentric. However, in other examples, different configurations may be used for one or more of first ferrule 14, second ferrule 16, and insulator 26. Insulator 26 may secure first ferrule 14 to second ferrule 16. For example, surfaces defined by insulator 26 may be joined, welded, adhered, or otherwise bonded to respective surfaces defined by first and second ferrules 14 and 16, such that insulator 26 secures first and second ferrules 14 and 16 at a fixed relative orientation.

IHC segment 13 also includes seal 28. Seal 28 may include a semi-soft or soft sealing material for providing a hermetic seal at at least one surface defined by IHC segment 13 to ultimately provide a hermetic seal to IHC assembly 12. The sealing material may include silicone, silicone rubber, fluorocarbons, fluorosilicone rubber, an elastomer, a thermoplastic elastomer, or any suitable moldable material. The silicone material may include a two-part, platinum-catalyzed, translucent silicone material with a predetermined durometer hardness. In some examples, the durometer hardness may be between 40 Shore A and 90 Shore A. For example, the durometer hardness may be 70 Shore A. In some examples, seal 28 consists of silicone rubber. The sealing material may be formed by allowing a mold material to set or cure. The mold material may include a mold composition that may be fluid to flow into and occupy a mold volume under first predetermined conditions, and that may solidify, cure, or set, under second predetermined conditions. For example, the mold material may include liquid silicone rubber that may be flowable to occupy a mold volume until it cures to form a seal substantially defined by the mold volume. The solidification, setting, or curing may be initiated by one or more of heat treatment, cooling, UV (ultraviolet) light exposure, pressure changes, formation of chemical bonds, or polymer cross-linking and network propagation, or by other suitable setting, curing, or solidification techniques. In some examples, seal 28 may be secured to IHC segment 13 by a primer or bonding agent. For example, at least a part of a surface defined by IHC segment 13 may be coated with a primer that secures seal 28 to the surface. The primer may include any suitable agent capable of bonding or securing seal 28 to IHC segment 13. In some examples, the primer may include a silicone-based primer.

Seal 28 may define a surface that substantially confirms to a predetermined surface defined by IHC segment 13, for example, an inner surface of IHC segment 13, as shown in FIG. 3. In some examples, seal 28 may define a relative flat surface and a relatively uniform thickness. In other examples, seal 28 may define a portion with a varying thickness, or a portion that defines a protrusion from seal 28. For example, as shown in FIG. 3, seal 28 may define a seal flange 29. In some examples, seal flange 29 may assist in securing a lead portion inserted in IHC assembly 12. Alternatively, or in addition, seal flange 29 may provide a seal to prevent shorting between contacts on a lead connected to IHC assembly 12 and contacts on defined by IHC assembly 12, and may aid in securing the lead while maintaining minimal insertion and withdrawal forces. In some examples, seal flange 29 may be provided with any suitable configuration. For example, seal flange 29 may include more than one protrusion.

IHC segment 13 may thus include IHC segment portion 13a, which includes first and second ferrules 14 and 16, and insulator 26. Seal 28 may be provided or formed on IHC segment portion 13a including first and second ferrules 14 and 16 and insulator 26, by molding a silicone portion onto IHC segment portion 13a to form IHC segment 13 shown in FIGS. 2 and 3. For example, IHC segment portion 13a may be disposed and secured within a mold assembly, and a seal formulation, for example, a liquid silicone rubber formulation, may be injected into the mold assembly to occupy and solidify within a predetermined mold volume to define seal 28.

However, mold assemblies and techniques used for molding seal 28 onto IHC segment portion 13a to form IHC segment 13 may present problems. For example, improperly controlled molding may lead to dimensional variability in IHC segment 13, for example, in overall height and axial alignment of the components of IHC segment 13. Insulator 26 bonding or securing the first and second ferrules 14 and 16 may be fragile, or susceptible to cracking, chipping, or shattering on exposure to high molding pressures or stresses. The first or second ferrules 14 or 16 may get damaged. Air may be introduced during the molding process, resulting in bubbles or pockets of trapped air in seal 28. Applied or injected sealing material may escape from a mold volume, resulting in "flash," or excess mold material attached to or protruding from a seal molded on the IHC segment portion. For example, flash can occur even with gaps as small as 0.0002 inches at mold volume surfaces during injection molding. Such flash may prevent proper assembly of IHC segments 13, or may compromise the hermetic seal provided by IHC assembly 12. Removing flash from a molded IHC segment may entail secondary operations steps that may increase manufacturing times and costs. Additionally, removing flash may be difficult because of the relatively small size of the IHC segments.

Providing an interference fit between the mold components, for example, between mold cores of a mold and a mold insert (for example, IHC segment portion 13a onto which seal 28 is molded) may reduce or eliminate flash and other problems. For example, a slight interference may provide a good shutoff to escaping mold material and prevent flash. However, an interference fit, while mitigating flash, may result in or exacerbate other problems. In particular, an interference fit may impart additional stresses on insulator 26 in IHC segment 13, and even a relatively slight interference fit, as small as 0.0004 inch, between IHC segment portion 13a including insulator 26 and the mold may cause insulator 26 to fracture.

Example mold assemblies and techniques according to the disclosure may be used to provide a seal on an internal hermetic connector (IHC) segment portion to form an IHC segment, while reducing or avoiding one or more problems associated with molding.

Figures 4A, 4B:
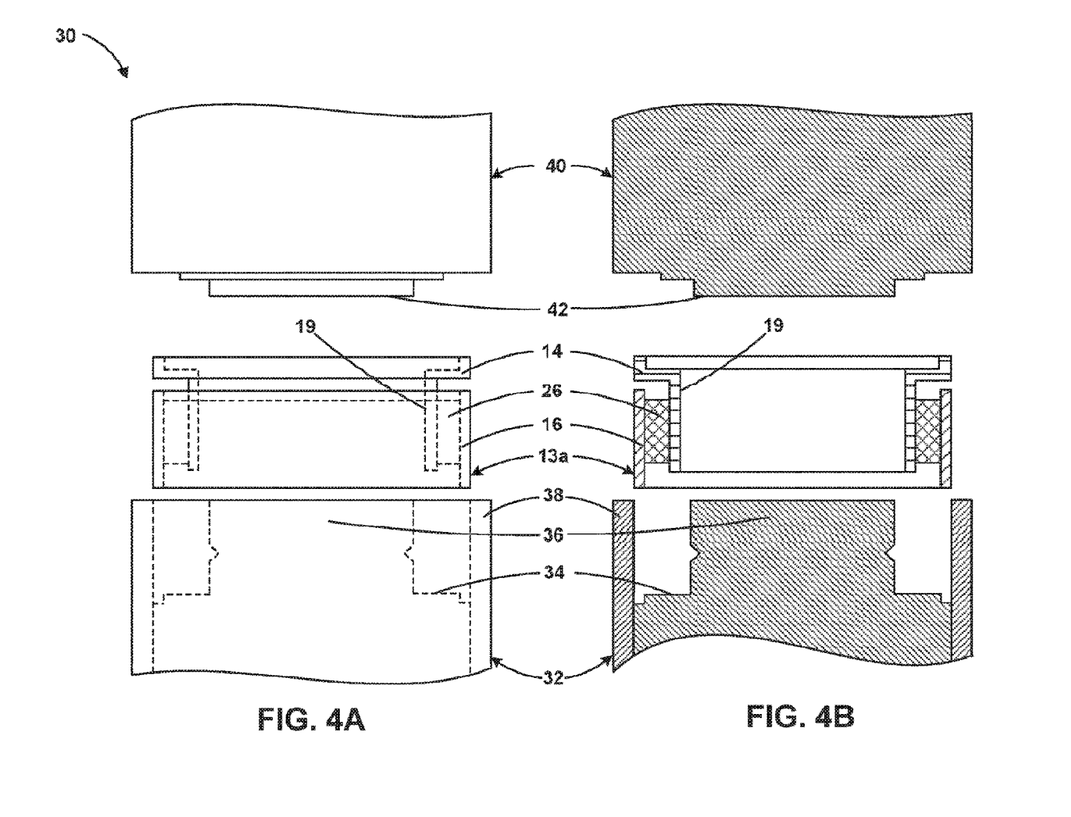
FIG. 4A is a schematic and conceptual exploded partial view of an example mold assembly including a first core and a second core for molding a seal on a mold insert including an internal hermetic connector segment portion.
FIG. 4B is a schematic and conceptual exploded cross-sectional partial view of the example mold assembly of FIG. 4A.

FIG. 4A is a schematic and conceptual exploded partial view of an example mold assembly 30 including a first core 32 and a second core 40 for molding seal 28 on a mold insert including internal hermetic connector segment portion 13a. FIG. 4B is a schematic and conceptual exploded cross-sectional partial view of example mold assembly 30 of FIG. 4A.

One or both of first or second cores 32 or 40 may include metal, alloy, ceramic, glass, polymer, compacted material, or any other suitable material or combinations thereof.

First core 32 defines an insert seat 34 configured to receive a mold insert. As shown in FIGS. 4A and 4B, the mold insert may include IHC segment portion 13a. Insert seat 34 may be defined by one or more regions or portions of a surface of first core 32. Insert seat 34 may include a flat surface region, a curved surface region, a polygonal surface region, or any surface region complementary to at least a portion of a surface of the mold insert. Insert seat 34 may thus retain the mold insert, for example, IHC segment portion 13a, in a fixed orientation relative to first core 32 or second core 40. In some examples, first core 32 defines a first core pin 36. First core pin 36 may be a protruding portion of first core 32, as shown in FIG. 4B. A portion or a surface of first core pin 36 may contact one or both of a portion of a surface of second core 40 or the mold insert. In some examples, a surface of first core pin 36 may by surrounded by a complementary surface of the mold insert, for example, a surface 19 defined by IHC segment portion 13a, to define at least a portion of a mold volume which may be occupied by a mold material, as described elsewhere in the disclosure. In some examples, first core 32 may include a first core sleeve 38 surrounding at least a portion of first core pin 36. One or both of first core pin 36 and first core sleeve 38 may define insert seat 34, for example, at least a portion of insert seat 34. In some examples, the mold insert may contact surfaces of one or both of first core pin 36 or first core sleeve 38 when secured on insert seat 34. First core sleeve 38 may be configured to restrict motion of first core 32 to motion along or about a longitudinal axis defined by first core sleeve 38. For example, first core sleeve 38 may be secured to first core pin 36 by an interference fit between an outer first core pin surface defined by first core pin 36 and an inner core sleeve surface defined by first core sleeve 38.

Second core 40 may define a pin portion 42 configured to contact at least a first insert surface defined by the mold insert. For example, the first insert surface may include a surface of IHC segment portion 13a adjacent pin portion 42, as shown in FIG. 4A or 4B. Thus, first core 32 and second core 40 may secure the mold insert, for example, IHC segment portion 13a, on seat insert 34 between one or more of first core pin 36, first core sleeve 38, or pin portion 42, when mold assembly 30 is assembled.

Figure 4C:
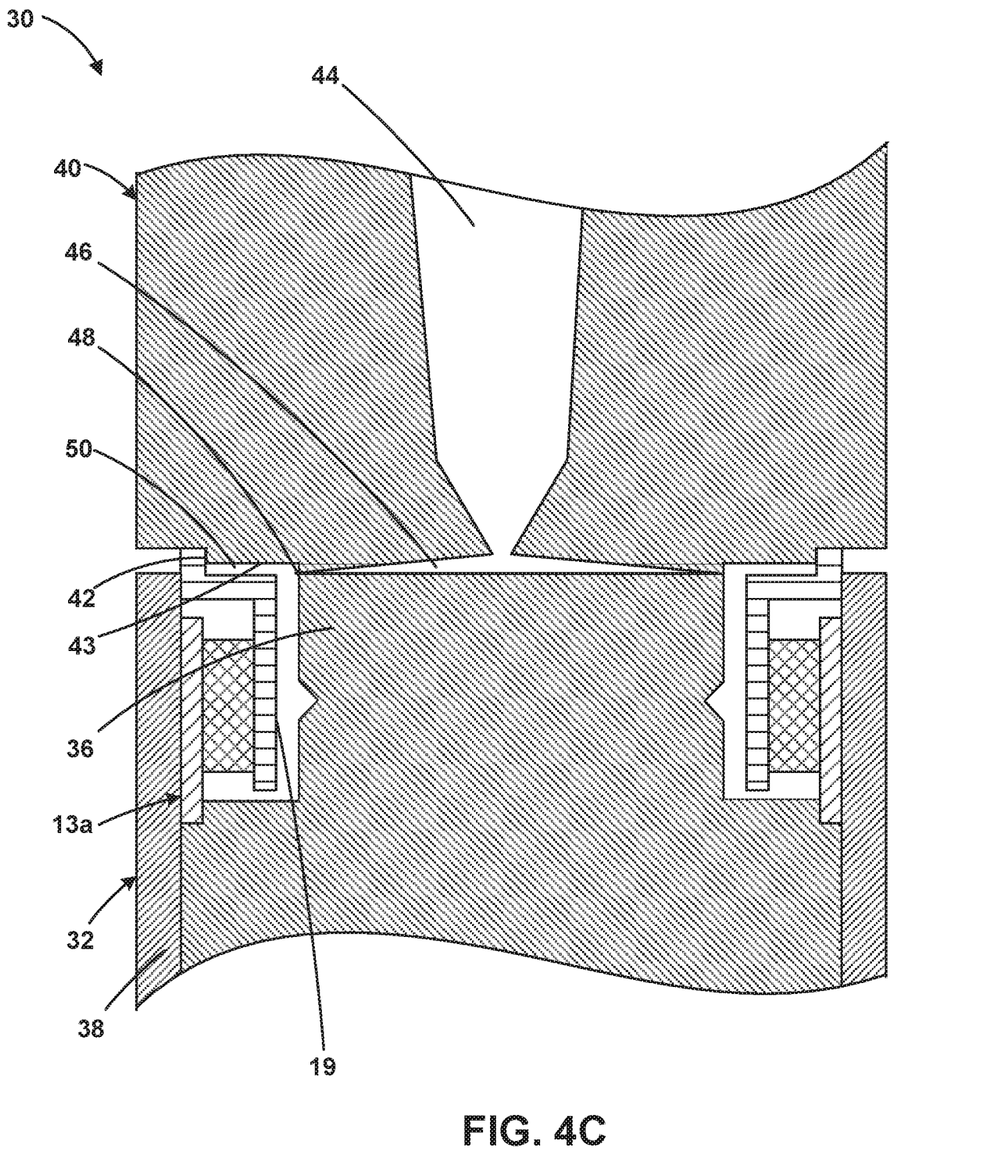
FIG. 4C is a schematic and conceptual partial cross-sectional view of the example mold assembly of FIG. 4A assembled with the mold insert secured between the first and the second cores.

FIG. 4C is a schematic and conceptual partial cross-sectional view of example mold assembly 30 of FIG. 4A assembled with the mold insert secured between first and second cores 32 and 40. For example, first core pin 36 of first core 32 abuts pin portion 42 defined by second core 40. When mold assembly 30 is assembled, one or more surfaces of surfaces defined by first core 32, second core 40, and the mold insert may define a mold volume 50. For example, surface 19 defined by IHC segment portion 13a, a surface 43 of pin portion 42, a surface of first core pin 36, and insert seat 34 may define mold volume 50, as shown in FIG. 4C. One or both of first core 32 and second core 42 may define a runner 44 fluidically connected to opening 48 of fan gate 46 to admit or inject mold material into mold volume 50. One or both of first core 32 and second core 40 may define fan gate 46 fluidically connected to one or both of mold volume 50 or runner 44 to admit mold material from runner 44 into mold volume 50. Thus, in some examples, mold assembly 30 may include the mold material occupying mold volume 50.

When mold assembly 30 is assembled, the relative orientation and alignment of first core 32 and second core 40 may determine stresses or forces applied to the mold insert, the orientation of the mold insert, and gaps or openings in mold volume 50 that may allow mold material to escape, resulting in flash formation. For example, if first core 32 and second core 40 are spaced or distanced apart beyond a predetermined threshold spacing, the mold insert may not be properly secured between first core 32 and second core 40, and may move when mold material is injected into or allowed to flow into mold volume 50. An increased spacing may also lead to gaps or openings between respective surfaces of first core 32, second core 40, and the mold insert. In contrast, reducing the spacing or distance between first core 32 and second core 40 may reduce gaps or openings, and may substantially mechanically or physically secure the mold insert within the assembly. However, reducing the spacing may increase in the stresses or forces exerted on the mold insert, for example, on IHC segment portion 13a, which may damage one or more components of IHC segment portion 13a, or may bend, fracture, shatter, or otherwise affect the integrity of one or more of first or second ferrules 14 or 16 or insulator 26. Further, relative misalignment of first core 32 and second core 40, for example, from relative tilting beyond a predetermined tolerance, may add to the stresses on the mold insert. For example, too much deflection may result in insulator 26 cracking or breaking the bond between insulator 26 and first or second ferrules 14 or 16.

Thus, maintaining predetermined geometric and stress tolerances within the mold assembly may help in reducing or avoiding one or more problems discussed in the disclosure. For example, securing second core 40 relative to first core 32 in a predetermined orientation subject to predetermined tolerances, for example, geometric tolerances such as relative spacing and alignment, may help maintain the mold insert in a secured position or orientation, reduce or avoid development of stresses beyond predetermined tolerances, or reduce or avoid gaps or openings that may lead to flash. The predetermined tolerances may include one or both of insert height of the mold insert, for example, of IHC segment portion 13a, and relative tilt between the first and second ferrules 14 and 16. For example, application of compressive forces or tilting forces by first or second core 32 or 40 that may push, pull, or tilt ferrules 14 or 16 beyond a range of acceptable tolerances may cause one or more of insulator 26 or ferrules 14 or 16 to break or deform. Mold assembly 30 may help to promote securing or maintaining one or more of first core 32, second core 40, and the mold insert within predetermined tolerances. Further, manufacturing variations in preparing different batches or samples of the mold insert may lead to variations in the relative spacing and tilting between components of the mold insert, for example, between first and second ferrules 14 and 16. These manufacturing variations may also change the forces and stresses ultimately applied to components of the mold insert when seated on insert seat 34. For example, mold assembly 30 in a first configuration for accommodating a first mold insert that substantially conforms to manufacturing tolerances may not sufficiently conform to a second mold insert that may deviate from manufacturing tolerances. Thus, if components of mold assembly 30 can accommodate manufacturing variations within predetermined manufacturing tolerances for the mold insert, for example, by slightly changing relative spacing and orientation between components of mold assembly 30, that may help with relieving stresses on the mold insert and in avoiding gaps and openings that may lead to flash formation.

Figure 5:
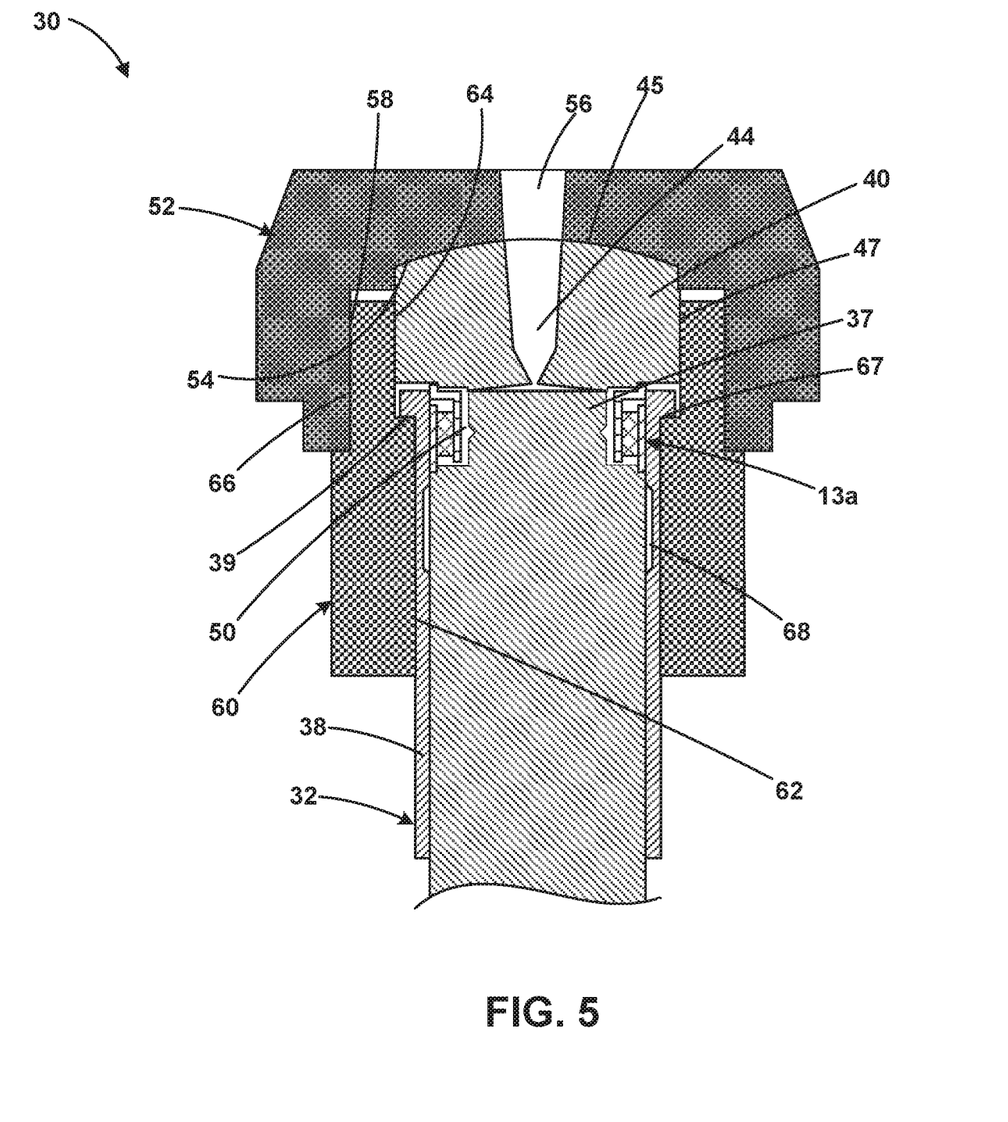
FIG. 5 is a schematic and conceptual partial cross-sectional view of an example mold assembly including a first core, a second core, a mold insert, a retaining cap, and a retaining sleeve.

FIG. 5 is a schematic and conceptual partial cross-sectional view of example mold assembly 30 including first core 32, second core 40, the mold insert (for example, IHC segment portion 13a), a retaining cap 52, and a retaining sleeve 60. In some examples, as shown in FIG. 5, second core 40 defines a curved end portion 45 opposing pin portion 42. Retaining cap 52 may be disposed about curved end portion 45 defined by second core 40. Retaining cap 52 may define a curved cap surface 54 in contact with curved end portion 45. In some examples, curved cap surface 54 of the retaining cap is substantially concave, and curved end portion 45 of second core 40 is substantially convex and conforms to curved cap surface 54. For example, curved cap surface 54 and curved end portion 45 may define a ball and socket-type joint. In some examples, curved cap surface 54 of retaining cap 52 and curved end portion 45 of second core 40 define a ball joint configured to allow second core 40 to pivot relative to retaining cap 52 while securing second core 40 at the predetermined orientation within the predetermined tolerances. In other examples, curved cap surface 54 and curved end portion may define other suitable complementary surfaces, for example, spheroidal, hyperbolic, or ellipsoidal surfaces.

Thus, in some examples, retaining cap 52 secures second core 40 at a predetermined orientation relative to first core 32 within predetermined tolerances. Further, the complementary curved end portion 45 and curved cap surface 54 may allow slight relative motion or realignment of second core 42 relative to first core 32 or the mold insert, which may assist with relieving, mitigating, or redistributing stresses or pressures so that stresses experienced by the mold insert are within predetermined tolerances. Providing retaining cap 52 in mold assembly 30 may help to avoid or reduce one or more problems described in the disclosure. Retaining cap 52 may include materials similar to those described with reference to first and second cores 32 and 40. Retaining cap 52 may define a second runner channel 56, such that second core 40 and retaining cap 52 together define runner 44 fluidically connected to mold volume 50 to admit mold material into mold volume 50.

In some examples, mold assembly 30 may include retaining sleeve 60 disposed between a surface defined by retaining cap 52 and one or both of first core 32 and second core

40. Retaining sleeve 60 may define a first inner sleeve surface 62 disposed about at least insert seat 34 of first core 32. In some examples, first inner sleeve surface 62 contacts an outer surface of first core 32, for example, an exterior surface of first core sleeve 38, as shown in FIG. 5. Retaining sleeve 60 may define a second inner sleeve surface 64 disposed about at least pin portion 42 of second core 40. Retaining sleeve may define an outer sleeve surface 66, wherein retaining cap 52 defines a retaining surface 58 contacting outer sleeve surface 66 of retaining sleeve 60. Retaining cap 52 may be secured to retaining sleeve 60 by an interference fit between retaining surface 58 and outer sleeve surface 66. In some examples, retaining cap 52 is secured to retaining sleeve 60 by a threaded fit between a first thread defined by retaining surface 58 and a second thread defined by outer sleeve surface 66.

In some examples, retaining sleeve 60 secures first core 32 to maintain the predetermined orientation of second core 40 relative to first core 32 within the predetermined tolerances. For example, retaining sleeve may secure one or more of first core 32, second core 40, and retaining cap 52 in predetermined orientations by one or both of an interference fit or a threaded fit at respective contacting surfaces, for example, at first inner sleeve surface 62, second inner sleeve surface 64, or outer sleeve surface 66. Retaining sleeve 60 may define additional features to provide a secure fit. For example, retaining sleeve 60 may define an annular landing 67, and first core 32 may define an annular lip 39, where annular landing 67 secures annular lip 39. In some examples, first core sleeve 38 of first core 32 defines annular lip 39, as shown in FIG. 5. Annular landing 67 may limit the relative longitudinal spacing between first core 32 and second core 40, for example, between first core pin 36 and pin portion 42. Annular landing 39 may be defined by sleeve 60 between first inner sleeve surface 62 and second inner sleeve surface 64.

Thus, one or both of retaining cap 52 and retaining sleeve 60 may help in holding one or more of the mold insert, first core 32, and second core, within predetermined relative orientations, while still allowing the mold insert, first core 32, and second core to slightly move within the range of tolerances to account for manufacturing variations which may cause slight geometric variations in the mold insert. For example, mold assembly 30 may accommodate for variations in mold insert height and tilt while allowing for adjustability in the shut off force being applied to the mold insert to avoid flashing. Thus, mold assembly 30 including one or both of retaining cap 52 and retaining sleeve 60 may reduce or avoid one or more problems associating with molding described in the disclosure. In some examples, one or both of retaining cap 52 or retaining sleeve 60 may be repositioned after placing the mold insert on insert seat 34 between first and second cores 32 and 40, for example, by releasing and re-securing the interference fit to adjust to variations in height of the mold insert, and the ball and socket joint-type configuration of retaining cap 52 and second core 40 may be adjusted or self-adjust to account for variations in tilt of the mold insert. At the same time, one or both of retaining cap 52 or retaining sleeve 60 may be repositioned to apply appropriate shut off forces at contacting surfaces of the mold insert, first core 32, and second core 40, to prevent formation of gaps or openings that may release mold material to avoid flash formation.

Thus, mold assembly 30 may maintain the clamping forces from the molding assembly independent of the forces applied to the mold insert within the mold assembly. Further, the amount of forces or stressed applied to the mold insert may be reduced even while providing sufficient shut off forces by securing mold components by interference or threaded fits. For example, mold clamping forces may be applied to retaining cap 52, while forces applied to the mold insert may be controlled by the threaded fit or interference fit between retaining cap 52 and retaining sleeve 60.

In some examples, air or another gas may be introduced into mold volume 50 with the mold material. Such air or gas may get trapped within mold volume 50, and ultimately into the mold material, resulting in voids, pockets, or bubbles in seal 28. To avoid accumulation of air or gas, in some examples, first core 32 may define at least one overflow vent 68 configured to remove or vent air from the mold volume. In some examples, one or both of first core sleeve 38 or first core pin 36 defines at least one overflow vent 68. At least one overflow vent 68 may include a plurality of fluidically connected vents, pores, channels to vent air or gas from mold volume 50 outside mold assembly 30. Fan gate 46 may have a ring gate design to feed the mold volume with a uniform packing pressure to the mold insert as the mold material solidifies to form seal 28, offering a more uniform shrink as seal 28 cools about and adjacent to IHC segment portion 13*a* in mold assembly 30, and during post cure processes. Ring gates, however, may tend to trap air due to the flow pattern as mold volume 50 fills with the mold material, especially in the case of molding small components such as IHC segment portion 13*a*. While a vacuum system may be used to remove air or gas, the vacuum system may be sufficient. Thus, in some examples, vent 68 may provide an overflow to removed substantially all air or gas from mold volume 50 and avoid formation of air pockets or bubbles in seal 28.

Thus, mold assembly 30 may be used to mold seal 28 on IHC segment portion 13*a* to form IHC segment 13, while reducing or avoiding problems such as flash formation, air bubbles, and breakage or damage to IHC segment 13. While mold assembly 30 is described with reference to a single mold insert, mold assembly may be used to provides seals on more than one mold insert, for example, by serially molding seals on a series of mold inserts. In some examples, an example assembly may include a plurality of mold assemblies, and respective seals may be provided on each of a plurality of mold inserts respectively disposed within respective mold assemblies of the plurality of mold assemblies.

Example techniques described with reference to FIG. 6 may be used to operate mold assembly 30. However, any other suitable techniques may also be used to operate mold assembly 30. Further, while mold assembly 30 was described with reference to an example mold insert including IHC segment, mold assembly can be used to provide a seal on, adjacent, or about any suitable mold insert.

Figure 6:
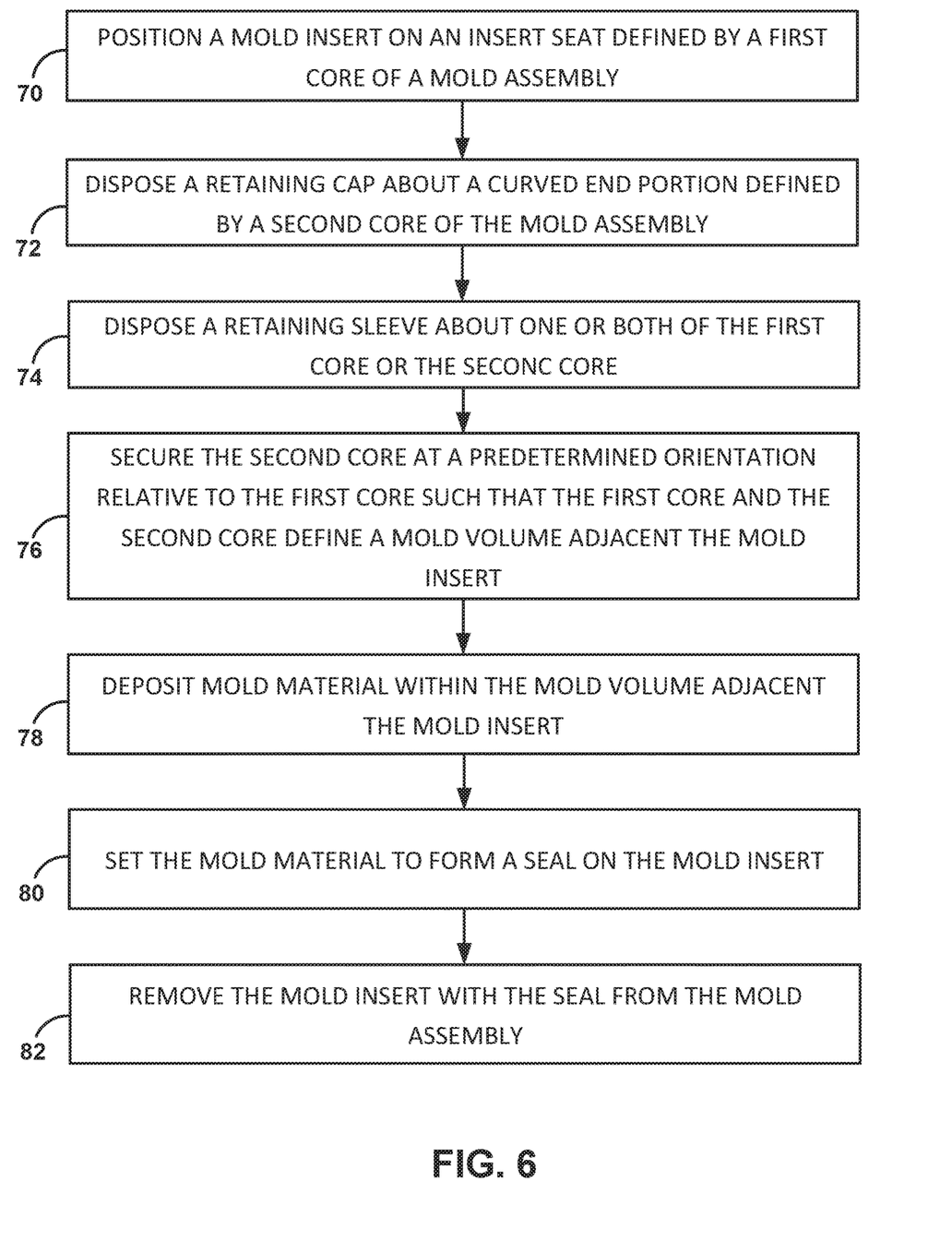
FIG. 6 is a flowchart illustrating an example technique for molding a seal on an internal hermetic connector segment portion.

FIG. 6 is a flowchart illustrating an example technique for molding seal 28 on a mold insert, for example, internal hermetic connector segment portion 13*a*. The example technique of FIG. 6 is described with reference to the mold assemblies shown in FIGS. 4A, 4B, 4C, and 5 only as an example. The example technique may be performed using other suitable mold assemblies. While the example technique is described with reference to an operator, an industrial robot or an automated or semi-automated assembly tool may be used to perform example techniques according to the disclosure, for example, by inspecting, manipulating, orienting, fitting, or securing, one or more components. The example technique of FIG. 6 may include positioning a mold insert on insert seat 34 defined by first core 32 of mold assembly 30 (70). In some examples, the example technique may include positioning the mold insert, for example, IHC segment portion 13a, on a surface or within a volume or chamber at least partly defined by first core 32. The positioning (70) may be performed by an operator, for example, manually, or semi-automatically or automatically, by an industrial robot. For example, the operator or industrial robot may inspect and orient first core 32 and the mold insert, and place the mold insert on first core 32 (70).

The example technique may include disposing retaining cap 52 about curved end portion 45 defined by second core 40 of mold assembly 30 (72). For example, an operator may substantially align retaining cap 52 about a center of second core 40, and secure retaining cap 52 about second core by threaded or interference fit. In some examples, the example technique includes disposing retaining sleeve 60 about one or both of first or second cores 32 or 40 (74). For example, an operator may orient retaining sleeve 60 about first or second core 32 or 40, and secure retaining sleeve 60 in contact with and about first or second core 32 or 40 by threaded or interference fit. The operator may dispose retaining cap 52 such that it is secured to one or both of second core 40 or retaining sleeve 60, or to first core 32, for example, via retaining sleeve 60, or by direct contact with first core 32. The example technique may include orienting one or both of first core 32 or second core 40 such that first core pin 36 defined by first core 32 abuts pin portion 42 defined by second core 40, and such that one or both of first core pin 36 and first core sleeve 38 surrounding at least a portion of first core pin 36 define the insert seat, as described with reference to FIG. 5.

The example technique may include securing second core 40 at a predetermined orientation relative to first core 32 within predetermined tolerances such that pin portion 42 defined by second core 40 contacts at least a first insert surface defined by the mold insert and such that first core 32 and second core 40 define mold volume 50 adjacent the mold insert (76). For example, the operator may use one or both of retaining cap 52 or retaining sleeve 60 to secure first core 32 to second core 40.

In some examples, the example technique further includes securing first core sleeve 38 to first core pin 36 by an interference fit or a threaded fit between an outer first core pin surface defined by first core pin 36 and an inner core sleeve surface defined by first core sleeve 38. In some examples, securing second core 40 at the predetermined orientation within predetermined tolerances relative to first core 32 includes disposing first inner sleeve surface 62 defined by retaining sleeve 60 about at least insert seat 34 of first core 32, disposing second inner sleeve surface 64 defined by retaining sleeve 60 about at least pin portion 42 of second core 40, and securing retaining surface 58 defined by retaining cap 52 about outer sleeve surface 66 of retaining sleeve 60 such that curved cap surface 54 defined by retaining cap 52 contacts curved end portion 45 defined by second core 40. Securing retaining surface 58 defined by retaining cap 52 about outer sleeve surface 66 defined by retaining sleeve 60 may include providing an interference fit or threading retaining surface 58 over outer sleeve surface 66. In some examples, the example technique further includes securing annular lip 39 defined by first core sleeve 38 or by first core 32 to annular landing 67 defined by retaining sleeve 60. In some examples, the operator may use one or more vises, clamps, grips, platforms, or other securement devices to secure one or both of first core 32 or second core 40.

The example technique may include depositing mold material within mold volume 50 adjacent the mold insert (78). For example, the operator may allow mold material to flow through runner 44 and fan gate 46 across opening or openings 48 into mold volume 50. In some examples, the example technique may include injection molding, and the operator may cause the mold material to be injected into mold volume 50 via runner 44 and fan gate 46, for example, at predetermined temperatures or pressures. The mold material may include a settable or curable mold composition that may cure or set under predetermined conditions (80) when occupying mold volume 50 to form seal 28 defined by mold volume 50 as described elsewhere in the disclosure. In some examples, the example technique may include one or both of maintaining a temperature or a pressure within mold volume 50 within a respective predetermined temperature range or a respective predetermined pressure range. For example, a first predetermined temperature or first predetermined pressure may maintain mold material occupying mold volume 50 in a fluid state until mold volume 50 is completely occupied, while a second predetermined temperature or second predetermined pressure may initiate setting, solidification, or curing of the mold material to eventually form seal 28 defined by mold volume 50.

After the setting, the example technique may include separating first core 32 and second core 40, or other components of mold assembly 30, and removing the mold insert including molded seal 28 from mold assembly 30 (82). For example, seal 28 may be molded on IHC segment portion 13a using example mold assemblies and techniques according to the disclosure to prepare IHC segment 13. IHC segments 13 may further be assembled to form IHC assembly 12 as described elsewhere in the disclosure.

Thus, example mold assemblies and techniques according to the disclosure may be used to mold seals on, about, or adjacent to medical device components, while mitigating, reducing, or avoiding problems associated with molding or overmolding such as flash formation and stress-induced cracking or breakage.

Various examples have been described. These and other examples are within the scope of the following claims.

What is claimed is:

1. A mold assembly comprising:
    a first core defining an insert seat configured to receive a mold insert;
    a second core defining a pin portion configured to contact at least a first insert surface defined by the mold insert, wherein the second core defines a curved end portion opposing the pin portion, and wherein the first core and the second core are configured to define a mold volume adjacent the mold insert; and
    a retaining cap disposed about the curved end portion defined by the second core, wherein the retaining cap defines a curved cap surface in contact with the curved end portion, and wherein the retaining cap is configured to secure the second core at a predetermined orientation relative to the first core within predetermined tolerances.

2. The mold assembly of claim 1, wherein the curved cap surface of the retaining cap is substantially concave; and wherein the curved end portion of the second core is substantially convex and conforms to the curved cap surface.

3. The mold assembly of claim 1, wherein the curved cap surface of the retaining cap and the curved end portion of the second core define a ball joint configured to allow the second core to pivot relative to the retaining cap while securing the second core at the predetermined orientation within the predetermined tolerances.

4. The mold assembly of claim 1, wherein the first core defines a first core pin, wherein the first core comprises a first core sleeve surrounding at least a portion of the first core pin, and wherein one or both of the first core pin and the first core sleeve define the insert seat.

5. The mold assembly of claim 4, wherein the first core pin abuts the pin portion defined by the second core.

6. The mold assembly of claim 4, wherein the first core sleeve is configured to restrict motion of the first core to motion along or about a longitudinal axis defined by the first core sleeve.

7. The mold assembly of claim 4, wherein the first core sleeve is secured to the first core pin by an interference fit between an outer first core pin surface defined by the first core pin and an inner core sleeve surface defined by the first core sleeve.

8. The mold assembly of claim 1, further comprising a retaining sleeve defining a first inner sleeve surface disposed about at least the insert seat of the first core and a second inner sleeve surface disposed about at least the pin portion of the second core, and wherein the retaining cap defines a retaining surface secured about an outer sleeve surface defined by the retaining sleeve.

9. The mold assembly of claim 8, wherein the retaining sleeve secures the first core to maintain the predetermined orientation of the second core relative to the first core within the predetermined tolerances.

10. The mold assembly of claim 8, wherein the retaining cap is secured to the retaining sleeve by an interference fit between the retaining surface and the outer sleeve surface.

11. The mold assembly of claim 8, wherein the retaining cap is secured to the retaining sleeve by a threaded fit between a first thread defined by the retaining surface and a second thread defined by the outer sleeve surface.

12. The mold assembly of claim 8, wherein the retaining sleeve defines an annular landing, and wherein the first core defines an annular lip, wherein the annular landing secures the annular lip.

13. The mold assembly of claim 12, wherein the first core sleeve of the first core defines the annular lip.

14. The mold assembly of claim 12, wherein the annular landing is between the first inner sleeve surface and the second inner sleeve surface.

15. The mold assembly of claim 1, wherein the first core defines at least one overflow vent configured to remove air from the mold volume.

16. The mold assembly of claim 15, wherein one or both of the first core sleeve or the first core pin defines the at least one overflow vent.

17. The mold assembly of claim 1, wherein the second core and the retaining cap define a runner fluidically connected to the mold volume to admit mold material into the mold volume.

18. The mold assembly of claim 17, wherein one or both of the first core and the second core define a fan gate fluidically connected to the mold volume and to the runner to admit mold material from the runner into the mold volume.

19. The mold assembly of claim 1, wherein one or both of the first core and the second core define a fan gate fluidically connected to the mold volume to admit mold material into the mold volume.

20. The mold assembly of claim 1, wherein the mold insert comprises a first ferrule, a second ferrule, and an insulator, wherein the insulator secures the first ferrule to the second ferrule, and wherein the insulator electrically isolates the first ferrule from the second ferrule.

21. The mold assembly of claim 1, wherein the mold insert comprises an internal hermetic connector segment.

22. The mold assembly of claim 1, further comprising the mold insert.

23. The mold assembly of claim 1, further comprising a mold material occupying the mold volume.

24. A method comprising:
positioning a mold insert on an insert seat defined by a first core of a mold assembly;
disposing a retaining cap about a curved end portion defined by a second core of the mold assembly;
securing the second core at a predetermined orientation relative to the first core within predetermined tolerances such that a pin portion defined by the second core contacts at least a first insert surface defined by the mold insert and such that the first core and the second core define a mold volume adjacent the mold insert; and
depositing mold material within the mold volume adjacent the mold insert.

25. The method of claim 24, further comprising allowing the mold material to set to form a molded seal secured to the mold insert.

26. The method of claim 24, further comprising maintaining one or both of a temperature or a pressure within the mold volume within a respective predetermined temperature range or a respective predetermined pressure range.

27. The method of claim 24, further comprising, after setting of the mold material:
separating the first core and the second core; and
removing the mold insert including the molded seal from the mold assembly.

28. The method of claim 24, further comprising orienting one or both of the first core or the second core such that a first core pin defined by the first core abuts the pin portion defined by the second core, and such that one or both of the first core pin and a first core sleeve surrounding at least a portion of the first core pin define the insert seat.

29. The method of claim 28, further comprising securing the first core sleeve to the first core pin by an interference fit between an outer first core pin surface defined by the first core pin and an inner core sleeve surface defined by the first core sleeve.

30. The method of claim 24, wherein securing the second core at the predetermined orientation within predetermined tolerances relative to the first core comprises:
disposing a first inner sleeve surface defined by a retaining sleeve about at least the insert seat of the first core;
disposing a second inner sleeve surface defined by the retaining sleeve about at least the pin portion of the second core; and
securing a retaining surface defined by the retaining cap about an outer sleeve surface of the retaining sleeve such that a curved cap surface defined by the retaining cap contacts the curved end portion defined by the second core.

31. The method of claim 30, wherein securing the retaining surface defined by the retaining cap about the outer sleeve surface defined by the retaining sleeve comprises providing an interference fit between the retaining surface and the outer sleeve surface.

32. The method of claim 30, wherein securing the retaining surface defined by the retaining cap about the outer sleeve surface defined by the retaining sleeve comprises threading the retaining surface over the outer sleeve surface.

33. The method of claim 30, further comprising securing an annular lip defined by the first core sleeve to an annular landing defined by the retaining sleeve.

\* \* \* \* \*